United States Patent
Rosenberger et al.

(10) Patent No.: US 6,376,438 B1
(45) Date of Patent: Apr. 23, 2002

(54) SKIN-COMPATIBLE HAND CLEANSER, ESPECIALLY A COURSE HAND CLEANSER

(75) Inventors: Volker Rosenberger, Kaarst; Andreas Klotz, Krefeld; Marcel Veeger, Krefeld; Beatrice Bruecher, Krefeld, all of (DE)

(73) Assignee: Stockhausen GmbH & Co. KG, Krefeld (DE)

( * ) Notice: Subject to any disclaimer, the term of this patent is extended or adjusted under 35 U.S.C. 154(b) by 0 days.

(21) Appl. No.: 09/529,417

(22) PCT Filed: Oct. 21, 1998

(86) PCT No.: PCT/EP98/06680

§ 371 Date: May 1, 2000

§ 102(e) Date: May 1, 2000

(87) PCT Pub. No.: WO99/22712

PCT Pub. Date: May 14, 1999

(30) Foreign Application Priority Data

Oct. 30, 1997 (DE) .......................... 197 48 921

(51) Int. Cl.⁷ ............................ A61K 7/50; C11D 7/50
(52) U.S. Cl. .................................. 510/139; 510/138
(58) Field of Search ............................ 510/138, 137, 510/139, 535

(56) References Cited

U.S. PATENT DOCUMENTS

| | | | | |
|---|---|---|---|---|
| 5,441,666 A | * | 8/1995 | Dotolo | 252/170 |
| 5,888,951 A | * | 3/1999 | Gagnebien et al. | 510/130 |
| 5,891,449 A | | 4/1999 | Daniel et al. | |
| 6,265,363 B1 | * | 7/2001 | Viscovitz | 510/130 |
| 6,294,179 B1 | * | 9/2001 | Lee et al. | 424/401 |

FOREIGN PATENT DOCUMENTS

| | | |
|---|---|---|
| DE | 40 09 534 | 9/1991 |
| DE | 40 38 076 | 6/1992 |
| DE | 41 29 986 | 3/1993 |
| DE | 92 12 734 | 3/1994 |
| DE | 43 35 933 | 4/1995 |
| EP | 0 691 127 | 1/1996 |
| WO | WO 96/02230 | 2/1996 |
| WO | WO 96/17590 | 6/1996 |
| WO | WO 96/32092 | 10/1996 |
| WO | WO 97/05857 | 2/1997 |

OTHER PUBLICATIONS

H. Tronnier, et al., Grosse Verlag, Berlin, pp. 75–108, "Haut und Beruf", 1989.

H.P. Fiedler, Editio Cantor Verlag Aulendorf 4th Edition, vol. 1, pp. 376 and 1029, "Lexikon der Hilfsstoffe Fuer Pharmazie, Kosmetik und Angrenzende Gebiete", 1996.

Peter J. Frosch, et al., Contact Dermatitis, pp. 73–81, "An Improved Technique for Epicutaneous Testing of Irritant and Allergic Reactions", 1979.

J.J. Kresken, BMV Berliner Medizinische Verlagsanstalt GmbH, vol. 67, No. 4, pp. 334,337,338, "Untersuchungen zur Irritationspotenz Geweblich Verwendeter Hautschutz–und Hautpflegepraeparate", 1992.

Peter J. Frosch, Principles of Cosmetics for the Dermatologist, pp. 5–12, "Irritancy of Soaps and Detergent Bars", 1982.

M. Puschmann, et al., Aertzliche Kosmetologie, vol. 13, pp. 225,226,228,231,232 and 234, "Hautvertraeglichkeitsnachweis Neuartiger Syndetpraeparate", 1983.

* cited by examiner

*Primary Examiner*—Yogendra N. Gupta
*Assistant Examiner*—John M Petruncio
(74) *Attorney, Agent, or Firm*—Oblon, Spivak, McClelland, Maier & Neustadt, P.C.

(57) ABSTRACT

The invention relates to hydrous liquid paste or cream-like hand cleansing agents without organic solvents, especially a course hand cleanser with a rubbing agent. Said cleansing agents are characterized by a content of 10 to 30 wt. % of at least one vegetable oil from the group of triglycerides, saturated and/or unsaturated fatty acids, of 10 to 30 wt % of a tenside comprised of a fatty alcohol ethoxylate, at least one fatty alcohol ether sulfate and/or a salt of a sulfonated fatty acid, 10 to 65 wt. % water, each referring to the composition of the cleansing agent, and optionally 1 to 30 wt. % of at least one abrasive. In addition, the hand cleanser optionally contains at least one viscosity building agent and optional additional cosmetic auxiliary, accessory and/or active agents.

10 Claims, No Drawings

SKIN-COMPATIBLE HAND CLEANSER, ESPECIALLY A COURSE HAND CLEANSER

The invention relates to hydrous, liquid, pasty or creamy hand cleansing agents having improved dermatological compatibility and to the use of said agents for removing extreme contaminations.

Coarse hand cleansers preferably are used in those cases where contaminations such as lacquers, fats, oils, lubricants, metal dusts, graphite, carbon black and the like are to be expected. For example, such cleansing agents are known according to H. Tronnier, J. Kresken, K. Jablonski, B. Komp, Haut und Beruf, Grosse Verlag, Berlin, 1989, pp. 75–108. Formulations containing an abrasive, a surfactant/surfactant mixture, thickening agents, and optionally, auxiliary agents to control consistency, appearance, odor, and stability, such as pigments, odorous substances, stabilizers, and preservatives are known in general. For particularly persistent contaminations, products added with organic solvents such as aliphatic hydrocarbons, terpenes, carboxylic esters of the dimethyl adipate, dimethyl glutarate, dimethyl succinate, and di-n-butyl adipate or di-isopropyl adipate types are available, such as described in DE 43 35 933 A1.

Referring to the industrial sector, the more frequently such products are applied on the skin (up to 6 times per day and more), the more clearly the detrimental effects of surfactants and particularly solvents come to the fore, namely, defatting and dehydration of the skin by destroying the hydro-lipid mantle of the skin. As a result, there is enhanced absorption of toxic and allergenic substances or infestation by microorganisms, or, as a consequence, toxic or allergic skin reactions occur.

More recently, coarse hand cleansers have become familiar which include a grape seed oil in addition to the surfactants coconut fatty acid monoethanolamide, cocamidopropyldimethylglycine, C9-11-Pareth-6 and sulfated castor oil. These agents are subject to restrictions with respect to their dissimilarity and their cleaning efficiency. Furthermore, the surfactants coconut fatty acid monoethanolamide and cocamidopropylbetaine are known to involve a sensitization risk.

The DE 44 24 210 A1 describes non-hydrous shower oils containing at least 45 wt.-% of an oil selected from the group of oils having a high content of triglycerides, saturated and/or unsaturated fatty acids, such as soya oil, sunflower oil, wheat germ oil, and 55 wt.-% at maximum of surfactants, preferably monoisopropanolaminelauryl ether sulfate, coconut fatty acid diethanolamide. These formulations involve the following drawbacks: 1. their cleaning efficiency is not adequate to remove extreme contaminations, and 2. they contain fatty acid mono- or diethanolamides which, according to Fiedler, Edito Cantor verlag, 4th edn., 1996, p. 376, are known to involve a sensitization risk.

Hydrous shower formulations are known from EP 0,769,292 A1 wherein, in addition to surfactant mixtures, colza oil or colza oil derivatives are used as skin care components. Due to their lacking cleaning efficiency, these agents neither are suited as coarse hand cleansers.

As a result of the above-described detrimental effects of conventional agents, the object therefore is to provide a hand cleansing agent which is highly skin-compatible in dermatological terms, preferably a coarse hand cleanser which, even when used several times a day on healthy skin, induces only minor dehydration of the skin. Furthermore, surfactants involving a sensitization risk should be excluded.

Amazingly and unpredictably according to prior art, hydrous, liquid, pasty or creamy hand cleansers free of solvents, particularly coarse hand cleansers can be obtained which accomplish the given object.

They are characterized by a content of a) 10–30 wt.-%, relative to the composition of the hand cleansing agent, of one or more vegetable oils from the group of triglycerides, saturated and/or unsaturated fatty acids, preferably triglycerides having an elevated percentage of unsaturated fatty acids, more preferably colza oil, soya oil and/or linseed oil;

b) 10–30 wt.-%, relative to the composition of the hand cleansing agent, of a surfactant composition containing
   α) at least one fatty alcohol ethoxylate,
   β) at least one fatty alcohol ether sulfate, and
   γ) at least one salt of a sulfurated, preferably sulfonated fatty acid;

c) 10–65 wt.-% of water, relative to the composition of the hand cleansing agent;

d) optionally 1–30 wt.-%, relative to the composition of the hand cleansing agent, of one or more abrasives, preferably plastic abrasive agents based on polyethylene or polyurethane, abrasive agents based on natural kernel and/or shell meals, preferably bleached natural shell and/or kernel meals such as $H_2O_2$-bleached meals of walnut shells, almond shells or hazelnut shells, meals of olive, apricot or cherry kernels, or any mixture of these shell and kernel meals, more preferably $H_2O_2$-bleached walnut shell meal, and/or beads of waxes, preferably jojoba waxes;

e) optionally one or more viscosity-building agents, preferably organophilic and/or hydrophilic layer silicates, with bentonites being particularly preferred, polysaccharides, preferably cellulose, guar meal and/or xanthans, modified polysaccharides, preferably cellulose ethers, carboxymethylcellulose and/or hydroxyethylcellulose, and/or inorganic electrolytes, preferably NaCl and/or $MgSO_4$;

f) optionally further cosmetic adjuvants, additives and/or active substances such as pH regulators, odorous substances, preservatives, such as organic acids, and antioxidants such as vitamin E acetate;

the sum of components a) through f) invariably being required to make 100 wt.-%.

Preferably, fatty alcohol ethoxylates having the structure

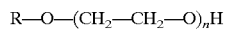

$$R-O-(CH_2-CH_2-O)_nH$$

wherein R represents a $C_8$–$C_{18}$, preferably $C_{10}$–$C_{16}$, more preferably $C_{11}$–$C_{14}$ saturated or unsaturated, branched or unbranched alkyl residue, and n represents an integer from 1 to 8, preferably 3–6, more preferably 5–7, are employed in component b) and, in particular, laureth-6 having R=$C_{12}$ and n=6 is used.

Fatty alcohol ether sulfates preferably to be used in component b) are those of general formula

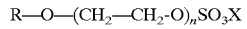

$$R-O-(CH_2-CH_2-O)_nSO_3X$$

wherein R represents a $C_{10}$–$C_{16}$, preferably $C_{11}$–$C_{14}$ saturated or unsaturated, branched or unbranched alkyl residue, n represents an integer from 1 to 6, preferably 1–4, and X represents $Na^+$, $NH_4^+$ or $Mg^{2+}$, and it is particularly preferred to use sodium lauryl ether sulfate (having $R=C_{12}$, $n=2-3$, and $X=Na^+$).

Alkali or alkaline earth salts Of $C_8$–$C_{30}$, preferably $C_{10}$–$C_{22}$ fatty acids, more preferably castor oil sulfates, and particularly the $Na^+$ or $NH_4^+$ sulfates are used as salts of sulfurated, preferably sulfonated fatty acids.

Monobrilliantöl® (Stockhausen GmbH & Co. KG) or Standapol SCO® (Henkel KGaA) is suited as castor oil sulfonate.

The surfactant compositions used according to the invention have no (or exceedingly low) sensitizing effect.

Surprisingly, it was found that the present object can only be accomplished if the provision is observed that the content of vegetable oil in the coarse hand cleanser composition is higher or equal to the content of fatty alcohol ethoxylates and the content of fatty alcohol ethoxylates is higher or equal to the content of the two components fatty alcohol ether sulfate and sulfurated fatty acids.

Accordingly, the content of 10–30 wt.-% of surfactant composition includes 5–28 wt.-%, preferably 7–25 wt.-% of component α, 1.9–15 wt.-%, preferably 3–10 wt.-% of component β and 0.1–10 wt.-%, preferably 0.5–6 wt.-% of component γ.

It is particularly preferred that the amount of 10–30 wt.-% of surfactant composition be comprised of 5–28 wt.-% of laureth-6, 1–10 wt.-% of sodium laureth sulfate (=sodium lauryl ether sulfate having 2 to 3 EO), and 1–10 wt.-% of castor oil sulfonate.

The hand cleansing agents according to the invention do not include any organic solvents.

The hand cleansing agents are produced in a continuous or batchwise fashion, using well-known devices. Suitable devices are tanks and stirrers, mixers and extruders.

The hand cleansing agents of the invention are used in such a way that the cleansing agent initially is spread over the skin, whereafter cleaning is continued using water, and completed by rinsing with water.

The hand cleansing agents of the invention exhibit good initial foaming capacity, good cleaning effect, and have improved dermatological compatibility compared to conventional products.

The invention will be explained with reference to the following Examples and examinations, such as the skin compatibility trial using the Duhring chamber test or the elbow bend wash test, skin dehydration using a corneometer, and cleaning efficiency using the hand wash test and stability test.

Test Methods:

Skin compatibility using the Duhring chamber test according to Frosch, P. J., Kligman, A. M., Contact Dermatites 5, p. 73, 1979; and Kresken, J. Wassilew, S. W., H+G4, p. 334, 1992

This method is an in vivo test model to check the skin compatibility of various test products in direct comparison. The products to be tested are applied on the subjects in air-impermeable aluminum chambers (Duhring chambers) on the volar side of their forearms on 5 consecutive days for 6 hours each time (5 hours on the last day) and on the same test area each time. The Duhring chambers are secured with plaster strips. In case of massive dermal effects, the test for the respective test zone is terminated even prior to reaching the total application time of 29 hours. What is assessed are skin irritations having formed, using the scale specified below, and the application time.

R=reddening (erythema): 0=no erythema, 4=massive erythema;
S=scaling: 0=no scaling, 4=massive scaling;
F=fissures: 0=no fissures, 4=massive fissures.

As criteria for assessment,
1. the irritation X as mean value of the sum of the irritation values R, S and F of n subjects,
2. the application time h as mean value of the tolerated application time in hours of n subjects are found.

Using these two values, the relative skin compatibility (A value) can be calculated according to the following formula:

$$\bar{A} = \frac{\bar{h}}{\sqrt{\bar{x}}}$$

Thus, it is possible by means of a value to describe a relation between the application time and an irritation having formed during said time. The following Table can be used as an aid in assessing the skin compatibility of the tested products:

| A value: | |
|---|---|
| >23 | excellent skin compatibility |
| 18–23 | high skin compatibility |
| 13–18 | good skin compatibility |
| 8–13 | satisfactory skin compatibility |
| 3–8 | sufficient skin compatibility |
| <3 | insufficient skin compatibility |

Skin compatibility examination according to the elbow bend wash test in accordance with P. J. Frosch, Principles of Cosmetics for the Dermatologist, P. Frost, S. Horwitz (ed.), pp. 5–12, Mosby, St. Louis (1982); M. Puschmann, J. Meyer-Rohn, Ärztl. Kosmetol. 13, 225 (1983).

*Inter alia*, the elbow bend wash test is used to examine the skin compatibility of coarse hand cleansers. This test is particularly suitable for assessing test products containing abrasive agents. Owing to the mechanically induced friction in the elbow bend, various products containing abrasive agents can be examined for skin irritation.

Controlled washings using the test products on the particularly sensitive skin of the elbow bend are carried out on four consecutive days until a subjective assessment of skin irritation is possible.

Test Material:

Cellulose pad for highly fluid products (e.g. PurZellin, Hartmann Company).

Subjects:

The test group consists of at least 6 males and females aged 18 to 60 years with healthy skin.

Test Products:

Non-flowable products are placed on the elbow bend in an undiluted state; if too dry, about 1 ml of water is added. Liquid products are dropped on cellulose and rubbed in.

Amounts used in test:

The test products are tested in amounts of 1 g or 1 ml.

Method:

The test products are applied in randomized fashion; application is as follows:

50% of subjects receive product A on the right and product B on the left;

50% of subjects receive product B on the right and product A on the left.

Coarse Hand Cleansers Containing Abrasive Agent:

Depending on the expected aggressiveness of the products, the test director decides the frequency of washings on all 4 days (once to twice per day). Testing is as follows:

The test product is placed on the elbow bend and spread by rubbing for 2 minutes using forefinger and middle finger. Thereafter, the product is allowed to rest on the elbow bend for 2 minutes and subsequently washed off.

The application of the test products is terminated prematurely as soon as a product causes intolerable skin irritations or massive burning on the skin.

Assessment:

Assessment is performed visually by the person operating the test 24 hours after the last tolerated washing in a rightleft comparison according to the following assessment criteria:

0=no reaction
1=weak, spotted reddening
2=moderate to medium reddening, slightly rough skin, slight scaling;
3=massive reddening in the center of the area, very rough skin, marked scaling, punctuated erosions.

In addition, the subjective sensation of the test persons is questioned according to the following scale:

0=no reaction
1=slight tension on skin
2=slight burning
3=massive, painful burning Assessment according to the above scoring scale directly permits a comparative statement as to the skin compatibility of the products. In case an assessment is between two assessment scores, rating in steps of 0.5 is possible for further differentiation.

Examination of Skin Dehydration Using a Corneometer:

Corneometer measurement is a non-invasive, capacitive measuring procedure for rating the moisture condition of the uppermost skin layers of the *Stratum corneum*. In subjects with healthy skin, said condition is largely determined by external effects.

Frequent skin cleansing gives rise to defatting of the skin and thus, to a reduction of moisture in the uppermost skin layers. Reduction of the moisture content of the skin represents a deterioration of the skin condition, causing an increased risk of eczema. This effect can be detected by measuring techniques using the CM 825 Corneometer supplied by the company Courage & Khazaka Electronic GmbH, Cologne.

Care must be taken that the measurements be conducted in a room having constant climatic conditions. Prior to measurement, the uncovered skin areas are to be conditioned for 15 minutes.

When using this method to support the Duhring chamber test assessment, the initial values ($C_0$) have to be determined prior to starting the test, and the final values ($C_n$) have to be determined upon completing the test. The area having demineralized water serves as a control area ($C_{cn}$; $C_{c0}$).

The change in skin moisture C is calculated as follows:

$$C = (C_n - C_0) - (C_{cn} - C_{c0})$$

Negative values indicate an increase of skin moisture, and positive values indicate a reduction of skin moisture.

Examination of Cleaning Power Using the Hand Wash Test:

The test model of the hand wash test using standardized dirt or lacquer provides information on the cleaning effect of the products to be examined. Using at least eight test persons, two products are subjected to a comparative examination. One precondition is that all test persons have a characteristic skin structure of their palms as a result of manual labor. Using one product at a time, the following test is performed in the morning and in the afternoon:

0.5 g of model dirt or 0.5 ml of lacquer is distributed on the palm and back of the hand and spread by rubbing for 45 seconds;
allow to dry for 1.5 minutes;
1.2 g of test product is applied and rubbed in;
add 1 ml of water and wash for 30 seconds;
again, add 1 ml of water and wash for 30 seconds;
rinse under flowing cold water;
visual rating of residual contamination (RC) on back of the hand and on palm according to scale below:
0 =clean; 5 =no cleaning effect (gradation in steps of 0.5 is possible).

The cleaning effect percentage is calculated according to the following formula:

$$\text{Cleaning effect} = \frac{10 - (RC_{palm} + RC_{back})}{10} \times 100 \ (\%)$$

$RC_{palm}$=mean value of residual contamination on palm in n measuring series (subjects)
$RC_{back}$ =mean value of residual contamination on back of hand in n measuring series (subjects)

As the determination of the cleaning effect has a broader variation range due to the test method, an absolute deviation of 5% between two measuring series is admissible.

Composition of model dirt:
Motor oil (Castrol) 54.15%
Vaseline 18.05%
Adeps Ianae 18.05%
Graphite 3.61%
Flame black 5.42%
Iron oxide ($Fe_2O_3$) 0.72%

Embodiments

Hand cleansing agents were produced according to the compositions specified in Table 1 by mixing all the components with stirring at room temperature. The agents were characterized by determining their skin compatibility, skin dehydration and cleaning effect against model dirt and lacquer. The determined results are summarized in Table 1.

As can be seen from Table 1, the agents of the invention in accordance with Examples 1–12 have improved skin compatibility and skin dehydration as compared to the agents according to Comparative Examples 13–16 which contain solvents.

As to the cleaning effect on the model dirt used, the formulations 1 and 2 exhibit a superior cleaning effect compared to the formulations 13–16 which contain solvents, and the formulations 3–12 exhibit a comparable cleaning effect.

As to the cleaning effect on the lacquer used, formulations 1 and 2 have a cleaning effect comparable to formulations 13 and 14 which contain DBE-2 or di-n-butyl adipate.

Surprisingly, as demonstrated by Example 5, the hand cleansing agents of the invention also exhibit an improved cleaning effect on model dirt and lacquer as compared to hand cleansing agents known from DE-C-40 38 076, particularly Example 6, and improved skin compatibility as determined by means of the elbow bend wash test.

| Formulation of Ex. | 1 | 2 | 3 | 4 | 5 | 6 | 7 | 8 | 9 |
|---|---|---|---|---|---|---|---|---|---|
| Formulation of Comp. Ex. | — | — | — | — | — | — | — | — | — |
| Colza oil | 30% | 30% | 30% | 20% | 20% | 20% | 10% | 10% | 10% |
| Grape seed oil | — | — | — | — | — | — | — | — | — |
| Soya oil | — | — | — | — | — | — | — | — | — |
| Linseed oil | — | — | — | — | — | — | — | — | — |
| Di-n-butyl adipate | — | — | — | — | — | — | — | — | — |
| DBE-2 | — | — | — | — | — | — | — | — | — |
| Isohexadecane | — | — | — | — | — | — | — | — | — |
| Terpene | — | — | — | — | — | — | — | — | — |
| Laureth-6 | 20% | 20% | 8% | 10% | 10% | 8% | 10% | 8% | 8% |
| Sodium laureth sulfate | 8% | 8% | 1% | 7% | 7% | 1% | 7% | 1% | 1% |
| Castor oil sulfate | 2% | 2% | 1% | 3% | 3% | 1% | 3% | 1% | 1% |

The compositions of the formulations are given in wt. %; all compositions include 5 wt. % of thickening agent (organophilic bentonite, carboxymethylcellulose, NaCl) and water, as well as additives of 1 wt. % (in total) of citric acid, preservatives, vitamin E acetate. The compositions 2, 3, 5 to 7, and 9 to 12, and Comparative Examples 13 to 17 include 13 wt. % of walnut shell meal.

| | 1 | 2 | 3 | 4 | 5 | 6 | 7 | 8 | 9 |
|---|---|---|---|---|---|---|---|---|---|
| Skin compatibility | 18–23 | 18–23 | 18–23 | 18–23 | 18–23 | 18–23 | 18–23 | 18–23 | 18–23 |
| Skin dehydration | 0 to −2 | 0 to −2 | 0 to −2 | 0 to −2 | 0 to −2 | 0 to −2 | 0 to −2 | 0 to −2 | 0 to −2 |
| Cleaning effect | | | | | | | | | |
| Model dirt | 95–98% | 95–98% | 90–95% | 85–90% | 90–95% | 90–95% | 90–95% | 90–95% | 90–95% |
| Lacquer | 90–95% | 90–95% | 80–85% | 80–85% | 85–90% | 80–85% | 85–90% | 83–88% | 80–85% |
| Skin compatibility Score | 0.4–0.6 | 0.8–1.0 | | 0.5–0.7 | 1.0–1.2 | | | | |
| (elbow bend wash test) subjective | 0.2–0.4 | 0.4–0.6 | | 0.2–0.4 | 0.4–0.6 | | | | |

| Formulation of Ex. | 10 | 11 | 12 | — | — | — | — | — |
|---|---|---|---|---|---|---|---|---|
| Formulation of Comp. Ex. | — | — | — | 13 | 14 | 15 | 16 | 17 |
| Colza oil | — | — | — | — | — | — | — | |
| Grape seed oil | 20% | — | — | — | — | — | — | |
| Soya oil | — | 20% | — | — | — | — | — | |
| Linseed oil | — | — | 20% | — | — | — | — | |
| Di-n-butyl adipate | — | — | — | 20% | — | — | — | |
| DBE-2 | — | — | — | — | 20% | — | — | |
| Isohexadecane | — | — | — | — | — | 20% | — | |
| Terpene | — | — | — | — | — | — | 20% | |
| Laureth-6 | 10% | 10% | 10% | 10% | 10% | 10% | 10% | |
| Sidium laureth sulfate | 7% | 7% | 7% | 7% | 7% | 7% | 7% | |
| Castor oil sulfate | 3% | 3% | 3% | 3% | 3% | 3% | 3% | |
| Skin compatibility | 18–23 | 18–23 | 18–23 | 12–17 | 12–17 | <10 | <10 | 18–23 |
| Skin dehydration | 0 to −2 | 0 to −2 | 0 to −2 | −4 to −8 | −12 to −16 | −4 to −8 | −12 to −16 | 0 to −2 |
| Cleaning effect | | | | | | | | |
| Model dirt | 90–95% | 90–95% | 90–95% | 90–95% | 90–95% | 90–95% | 90–95% | 80–85% |
| Lacquer | 80–85% | 80–85% | 80–85% | 90–95% | 90–95% | 80–85% | 80–85% | 70–75% |
| Skin compatibility Score | | | | | | | | 1.2–1.4 |
| (elbow bend wash test) subjective | | | | | | | | 0.5–0.7 |

*Comparative Example 17 corresponds to Example 6 of DE-C-40 38 076.

What is claimed is:

1. A hydrous, liquid, pasty or creamy hand cleansing agent, which does not contain any organic solvent and comprises:
   (a) 10–30 wt.-%, relative to the composition of the hand cleansing agent, of one or more vegetable oils selected from the group consisting of triglycerides and saturated and/or unsaturated fatty acids;
   (b) 10–30 wt.-%, relative to the composition of the hand cleansing agent, of a surfactant composition containing:
      ($\alpha$) at least one fatty alcohol ethoxylate,
      ($\beta$) at least one fatty alcohol ether sulfate, and
      ($\gamma$) at least one salt of a sulfurated fatty acid;
   (c) 10–65 wt.-% of water, relative to the composition of the hand cleansing agent;
   (d) optionally, 1–30 wt.-%, relative to the composition of the hand cleansing agent, of one or more abrasives;
   (e) optionally, one or more viscosity-building agents; and
   (f) optionally, further cosmetic adjuvants, additives and/or active substances; wherein the sum of components (a) through (f) is 100 wt.-%, and wherein the content of component (a) is higher or equal to the content of fatty alcohol ethoxylates ($\alpha$), and the content of fatty alcohol ethoxylates ($\alpha$) is higher or equal to the content of the two components ($\beta$) and ($\gamma$) in the composition of the hand cleansing agent.

2. The hand cleansing agent according to claim 1, wherein the triglycerides have an elevated percentage of unsaturated fatty acids.

3. The hand cleansing agent according to claim 1, wherein the surfactant composition (b) contains:
   fatty alcohol ethoxylates represented by the formula:

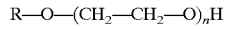
   $$R-O-(CH_2-CH_2-O)_nH$$

wherein R represents a $C_8$–$C_{18}$, saturated or unsaturated, branched or unbranched alkyl residue, and n represents an integer from 1 to 8, fatty alcohol ether sulfates represented by the formula:

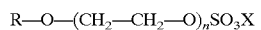
   $$R-O-(CH_2-CH_2-O)_nSO_3X$$

wherein R represents a $C_{10}$–$C_{16}$ saturated or unsaturated, branched or unbranched alkyl residue, n=1–6, and X represents $Na^+$, $NH_4^+$ or $Mg^{2+}$; and
   alkali, alkaline earth or ammonium salts of $C_8$–$C_{30}$ sulurated fatty acids.

4. The hand cleansing agent according to claim 3, wherein (b) comprises laureth-6, sodium lauryl ether sulfate and sodium or ammonium castor oil sulfonate.

5. The hand cleansing agent according to claim 1, wherein the surfactant composition (b) is comprised of 5–28 wt.-% of ($\alpha$), 1.9–15 wt.-%, of ($\beta$) and 0.1–10 wt.-% of ($\gamma$), wherein the sum of components ($\alpha$) through ($\gamma$) is 10–30 wt.-%.

6. The hand cleansing agent according to claim 1, wherein the abrasives are plastic abrasive agents based on polyethylene or polyurethane or abrasive agents based on natural kernel and/or shell meals.

7. The hand cleansing agent according to claim 6, wherein the abrasives are $H_2O_2$-bleached meal of walnut shells orjojoba wax beads.

8. The hand cleansing agent according to claim 1, wherein the viscosity-building agents are selected from the group consisting of organophilic and/or hydrophilic layer silicates, polysaccharides, modified polysaccharides, and inorganic electrolytes.

9. The hand cleansing agent according to claim 1, wherein the cosmetic adjuvants, additives and/or active substances are selected from the group consisting of pH regulators, odorous substances, preservatives, preferably organic acids, and antioxidants.

10. The hand cleansing agent according to claim 1, wherein (a) comprises colza oil, (b) comprises a mixture of laureth-6, sodium laureth sulfate and castor oil sulfonate as component b), (d) comprises bleached walnut shell meal as component d), (e) comprises bentonite, carboxymethylcellulose and sodium chloride as component e), and (f) comprises citric acid, preservatives, vitamin E acetate, and perfume.

* * * * *